US012782356B2

(12) United States Patent
Ueda et al.

(10) Patent No.: US 12,782,356 B2
(45) Date of Patent: Nov. 3, 2026

(54) SUGAR CHAIN SPECIFIC TO PROSTATE CANCER, AND TEST METHOD USING SAME

(71) Applicant: JAPANESE FOUNDATION FOR CANCER RESEARCH, Tokyo (JP)

(72) Inventors: Koji Ueda, Tokyo (JP); Yoshimi Haga, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 964 days.

(21) Appl. No.: 17/259,264

(22) PCT Filed: Jul. 5, 2019

(86) PCT No.: PCT/JP2019/026858
§ 371 (c)(1),
(2) Date: Jan. 11, 2021

(87) PCT Pub. No.: WO2020/013097
PCT Pub. Date: Jan. 16, 2020

(65) Prior Publication Data
US 2021/0278410 A1 Sep. 9, 2021

(30) Foreign Application Priority Data
Jul. 11, 2018 (JP) ................................ 2018-131774

(51) Int. Cl.
*G01N 33/57555* (2026.01)
*G01N 33/68* (2006.01)

(52) U.S. Cl.
CPC ... *G01N 33/57555* (2026.01); *G01N 33/6893* (2013.01); *G01N 2333/96455* (2013.01);
(Continued)

(58) Field of Classification Search
CPC ......... G01N 33/57434; G01N 2400/00; G01N 2440/38; G01N 2560/00;
(Continued)

(56) References Cited

U.S. PATENT DOCUMENTS 8,653,448 B1 * 2/2014 Ueda ...................... H01J 49/00 250/292
8,822,917 B2 9/2014 Ueda et al.
(Continued)

FOREIGN PATENT DOCUMENTS

EP 2 161 571 6/2012
JP 2002-055108 2/2002
(Continued)

OTHER PUBLICATIONS

Yabu in Occurrence of free deaminoneuraminic acid (KDN)-containing complex-type N-glycans in human prostate cancers. 2012 (Year: 2012).*
(Continued)

*Primary Examiner* — Rebecca M Fritchman
(74) *Attorney, Agent, or Firm* — Rankin, Hill & Clark LLP

(57) ABSTRACT

Provided is a test method for identifying prostate cancer by analyzing a sugar chain modifying PSA in a specimen, and detecting an abundance of a multisialylated LacdiNAc structure, in particular Glycan ID: 7512, Glycan ID: 7603, Glycan ID: 7612, and/or Glycan ID: 7613. Furthermore, calculation of PSA G-index from relative abundance(s) of Glycan ID: 7512 and/or Glycan ID: 7603 enables detection of prostate cancer with good specificity even in a patient having a PSA value in a gray zone.

12 Claims, 5 Drawing Sheets

(52) U.S. Cl.
CPC ..... *G01N 2400/00* (2013.01); *G01N 2400/38* (2013.01); *G01N 2440/38* (2013.01); *G01N 2560/00* (2013.01)

(58) Field of Classification Search
CPC ..... G01N 2333/96455; G01N 2400/38; G01N 2800/56
See application file for complete search history.

(56) References Cited

U.S. PATENT DOCUMENTS

2004/0253651 A1* 12/2004 Saarinen ................. A61P 35/00 536/53
2011/0236995 A1* 9/2011 Hirano ............. G01N 33/57469 436/64
2011/0294141 A1* 12/2011 Yamashita ....... G01N 33/57434 435/226
2016/0069884 A1* 3/2016 Zhang .............. G01N 33/57434 514/789

FOREIGN PATENT DOCUMENTS

| | | |
|---|---|---|
| JP | 2010-091308 | 4/2010 |
| JP | 2011-137754 | 7/2011 |
| JP | 2011-529184 | 12/2011 |
| JP | 2013-076666 | 4/2013 |
| JP | 2014-66704 | 4/2014 |
| WO | 2009/008381 | 1/2009 |
| WO | 2010/011357 | 1/2010 |
| WO | 2010/064683 | 6/2010 |
| WO | 2010/090264 | 8/2010 |

OTHER PUBLICATIONS

Lee in Comphrehensive N-Glycome profiling of cultered human epithelial breast cells indentifies unique secretome N- glycosylation signatures enabling tumorigenic subtype classification. 2014 (Year: 2014).*
Li in Detection and Verification of Glycosylation Patterns of Glycoproteins from Clinical Specimens Using Lectin Microarrays and Lectin-Based Immunosorbent Assays. 2011 (Year: 2011).*
Taberes.Different glycan structures in prostate-specific antigen from prostate cancer sera in relation to seminal plasma PSA (Year: 2006).*
Fukushima.α1,2-Fucosylated and β-N-acetylgalactosaminylated prostate-specific antigen as an efficient marker of prostatic cancer (Year: 2009).*
Catalona et al., "Use of the Percentage of Free Prostate-Specific Antigen to Enhance Differentiation of Prostate Cancer From Benign Prostatic Disease", JAMA, May 20, 1998, vol. 279, No. 19, pp. 1542-1547; discussed in specification.
Loeb et al., "The Prostate Health Index Selectively Identifies Clinically Significant Prostate Cancer", J Urol., Apr. 2015, vol. 193, pp. 1163-1169; discussed in specification.
Wei et al., "Can Urinary PCA3 Supplement PSA in the Early Detection of Prostate Cancer?", Journal of Clinical Oncology, Dec. 20, 2014, vol. 32, No. 36, 8 pages; discussed in specification.
Schmid et al., "Urinary Prostate Cancer Antigen 3 as a Tumour Marker: Biochemical and Clinical Aspects", Advances in Cancer Biomarkers, Advances in Eperimental Medicine and Biology, 2015, vol. 867, pp. 277-289; discussed in specification.
Wang et al., "Diagnostic ability of %p2PSA and prostate health index for aggressive prostate cancer. a meta-analysis", Scientific Reports, 2014, vol. 4, pp. 1-8; discussed in specification.
Vlaeminck-Guillem et al., "Urinary Prostate Cancer 3 Test: Toward the Age of Reason?", Urology, 2010, vol. 75, pp. 447-453; discussed in specification.
Wada, "Glycan Profiling: Label-Free Analysis of Glycoproteins", Methods in Molecular Biology, 2013, vol. 951, pp. 245-253; discussed in specification.
Toyama et al., "Quantitative Structural Characterization of Local N-Glycan Microheterogeneity in Therapeutic Antibodies by Energy-Resolved Oxonium Ion Monitoring", Analytical Chemistry, 2012, 8 pages; discussed in specification.
English translation of Written Opinion of the International Searching Authority dated Oct. 8, 2019, Application No. PCT/JP2019/026858, 5 pages.
Extended European Search Report dated Jul. 5, 2021, Application No. 19 834 011.9, 8 pages.
Chikara Ohyama et al., "Carbohydrate structure and differential binding of prostate specific antigen to Maackia amurensis lectin between prostate cancer and benign prostate hypertrophy", Glycobiology, Mar. 24, 2004, vol. 14, No. 8, pp. 671-679.
Guinevere S. M. Kammeijer et al., "An In-Depth Glycosylation Assay for Urinary Prostate-Specific Antingen", Analytical Chemistry, Mar. 4, 2018, vol. 90, pp. 4414-4421.
Kazuhisa Hagiwara et al., "Wisteria floribunda Agglutinin and Its Reactive-Glycan-Carrying Prostate-Specific Antigen as a Novel Diagnostic and Prognostic Marker of Prostate Cancer", International Journal of Molecular Sciences, Jan. 26, 2017, vol. 18; 16 pages.
Tomokazu Ishikawa et al. "An Automated Micro-Total Immunoassay System for Measuring Cancer-Associated α2,3-linked Sialyl N-Glycan-Carrying Prostate-Specific Antigen May Improve the Accuracy of Prostate Cancer Diagnosis", International Journal of Molecular Sciences, Feb. 22, 2017, vol. 18; 15 pages.

* cited by examiner

SUGAR CHAIN SPECIFIC TO PROSTATE CANCER, AND TEST METHOD USING SAME

TECHNICAL FIELD

The present invention relates to an index for prostate cancer diagnosis and a test method using the same.

BACKGROUND ART

Prostate cancer is a cancer specific for men and frequently occurred in the elderly, and about 90% or more of the patients are 60 years or older. With the increase of the elderly, the number of the patients is increasing. According to the projected cancer cases by part in male in 2017 in the "Cancer Registry and Statistics" by Cancer Information Service, National Cancer Center, the number of patients newly suffering from prostate cancer is 86,100, ranking third in the number of cases following stomach and lung cancers, and is predicted to increase further with aging in the future. Prostate cancer progresses relatively slowly in many cases, and therapies such as radiation therapy and endocrine (hormone) therapy, in addition to surgery, can be taken as effective measures. Thus, prostate cancer is treatable if detected early.

Prostate cancer has been diagnosed by measuring prostate specific antigen (PSA) in blood. PSA screening is a blood test, thus it is minimally invasive, and has high sensitivity. PSA screening has thus been incorporated and performed in medical checkup as a test for prostate cancer.

However, PSA is produced in prostate epithelium, and is overproduced in not only prostate cancer, but also other prostate diseases such as prostatic hypertrophy and prostatitis. Thus, false positives often occur in patient screenings with PSA, which is considered a problem. PSA has a cutoff value of 4 ng/ml. When PSA value in blood is greater than or equal to the value, prostate cancer is suspected, and diagnosis by transrectal prostate palpation, transrectal echo, or transperineal prostate needle biopsy becomes necessary. For the range referred to as a "gray zone" with a PSA value of 4 to 10 ng/ml, there is a result that about 70% of the subjects do not suffer from cancer, and 50% of the subjects do not suffer from cancer even their PSA values are 10 to 20 ng/ml (Non Patent Literature 1).

When the diagnosis is determined by transperineal prostate needle biopsy, it is necessary to perform 10 to 12 tissue samplings in the first biopsy after hospitalization and anesthesia, and it is accompanied with severe pain. Partly because of the high false positive rate, many patients with PSA values in the range of the gray zone do not have prostate biopsies even when they are recommended for secondary examination in medical checkup, so they often miss opportunities for early detection. In fact, there are statistics showing that only about 30 to 50% of those who were determined to be PSA positive at medical checkup centers receive prostate biopsy.

Conventionally, methods that increase specificity of PSA test, distinguish prostate cancer from prostatic hypertrophy and specifically detect prostate cancer have been proposed (Non Patent Literatures 2 to 4, Patent Literatures 1 to 8). As PSA tests, Food and Drug Administration (FDA) has already approved prostate health index (PHI) (Non Patent Literature 2) and prostate cancer antigen 3 (PCA3) examination (Non Patent Literatures 3, 4). Patent Literatures 1 to 5 describe methods of contacting PSA with lectin that recognizes specific binding sialic acids, and performing examination using the binding properties with lectin. Patent Literatures 6 to 8 disclose methods of analyzing sugar chain structures by mass spectrometry to detect prostate cancer.

CITATION LIST

Patent Literature

Patent Literature 1: Japanese Patent Laid-Open No. 2002-55108
Patent Literature 2: Japanese Patent Laid-Open No. 2010-91308
Patent Literature 3: Japanese Translation of PCT International Application Publication No. 2011-529184
Patent Literature 4: Japanese Patent Laid-Open No. 2013-076666
Patent Literature 5: International Publication No. WO 2010/090264
Patent Literature 6: International Publication No. WO 2009/008381
Patent Literature 7: International Publication No. WO 2010/064683
Patent Literature 8: Japanese Patent Laid-Open No. 2011-137754
Patent Literature 9: Japanese Patent Laid-Open No. 2014-066704

Non Patent Literature

Non Patent Literature 1: Catalona W J., et al., 1998, Jama, Vol. 279, pp. 1542-1547
Non Patent Literature 2: Loeb, S. et al., 2015, J. Urol. Vol. 193, pp. 1163-1169.
Non Patent Literature 3: Wei., J. T. et al., 2014, J. Clin. Oncol., Vol. 32, pp. 4066-4072.
Non Patent Literature 4: Schmid, M. et al., 2015, Advances in experimental medicine and biology, Vol. 867, pp. 277-89
Non Patent Literature 5: Wang, W. et al., 2014, Sci. Rep. Vol. 4, p. 5012
Non Patent Literature 6: Vlaeminck-Guillem V. et al., 2010, Urology. Vol. 75, pp. 447-453.
Non Patent Literature 7: Wada, Y. 2013, Methods in molecular biology (Clifton, NJ), Vol. 951, pp. 245-253.
Non Patent Literature 8: Toyama, A. et al., 2012, Anal. Chem. Vol. 84, pp. 9655-9662

SUMMARY OF INVENTION

Technical Problem

All of the examination methods disclosed in the above literatures are, however, problematic in specificity or sensitivity, and any of them failed to specifically identify prostate cancer. PHI is high in sensitivity of 85%, but low in specificity of 45%, and cannot specifically identify prostate cancer (Non Patent Literature 5). PCA3 is an excellent examination method in that it is not affected by diseases other than cancer such as prostatic hypertrophy and prostatitis, but the results of four clinical tests showed that it is low in sensitivity, which is 53 to 84%, and insufficient to detect prostate cancer in the patients having PSA values of the gray zone (Non Patent Literature 6).

In the methods described in Patent Literatures 1 to 5, prostate cancer is diagnosed by analyzing saccharides modifying PSA by the binding properties to lectin. However, A problem is that lectin has low affinity compared to antibodies, leading to low sensitivity. Another problem is that lectin does not detect only saccharides modifying target PSA, and also binds to saccharides modifying other proteins. Thus, the methods using lectin cannot completely eliminate false positives.

Patent Literatures 6 to 8 disclose methods of identifying prostate cancer and prostatic hypertrophy by mass spectrometry. Patent Literature 6 describes a method for detecting prostate cancer by a ratio of fucose-bound sugar chains to fucose-unbound sugar chains, Patent Literature 7 describes that by an amount of sugar chains having LacdiNAc, and Patent Literature 8 describes that by the presence or absence of three or more sugar chains having LacdiNAc. However, none of them were enough to eliminate false positives because they are low in specificity.

PSA has been modified by sugar chains, and it has been reported that the type of modifying saccharides is correlates with prostate disease. However, accurate distinguishing between prostate cancer and prostatic hypertrophy has not achieved yet. An object of the present invention is to provide a method for accurately detecting prostate cancer even in a range of the gray zone in which a slight increase in PSA is observed, and to provide an index for identifying prostate cancer.

Solution to Problem

The present invention relates to the following method for testing prostate cancer and index for detecting prostate cancer. Furthermore, it relates to a marker for evaluating grade (malignancy).

(1) A test method of prostate cancer, comprising:

analyzing a sugar chain modifying PSA in a specimen; and analyzing a multisialylated LacdiNAc structure.

(2) The test method of prostate cancer according to (1), comprising:

analyzing a sugar chain modifying PSA in a specimen; and analyzing relative abundance(s) of Glycan ID: 7512, Glycan ID: 7603, Glycan ID: 7612, and/or Glycan ID: 7613.

(3) The test method of prostate cancer according to (2), wherein the relative abundances of Glycan ID: 7512 and Glycan ID: 7603 are analyzed by logistic analysis.

(4) The test method of prostate cancer according to (2), comprising:

substituting the relative abundances of Glycan ID: 7512 and Glycan ID: 7603 into the following formula 1:

[Expression 1]

$$\log_e(p/(1-p)) = -5.85 + 4.72x_1 + 0.80x_2 \quad \text{(Formula 1)}$$

wherein p represents a value of PSA G-index; $x_1$ represents a relative abundance of Glycan ID: 7512, and $x_2$ represents a relative abundance of Glycan ID: 7603.

(5) The test method of prostate cancer according to any one of (1) to (4), wherein the specimen is blood, serum, plasma, or urine.

(6) The test method of prostate cancer according to any one of (1) to (5), wherein the specimen is a specimen obtained from a patient having a PSA value of 4 to 10 ng/ml.

(7) The test method of prostate cancer according to any one of (1) to (6), wherein the sugar chain is analyzed using an oxonium monitoring method.

(8) An index for identifying prostate cancer, which is a PSA G-index determined by the following formula 1:

[Expression 2]

$$\log_e(p/(1-p)) = -5.85 + 4.72x_1 + 0.80x_2 \quad \text{(Formula 1)}$$

wherein p represents a value of PSA G-index; $x_1$ represents a relative abundance of Glycan ID: 7512, and $x_2$ represents a relative abundance of Glycan ID: 7603.

(9) A method for testing a grade of prostate cancer, comprising:

analyzing a sugar chain modifying PSA in a specimen; and analyzing relative abundance(s) of at least one or more of Glycan ID: 7512, Glycan ID: 7603, Glycan ID: 3401, and/or Glycan ID: 5602.

(10) The test method according to (9), wherein the specimen is blood, serum, plasma, or urine.

(11) The test method according to (9) or (10), wherein the analysis uses an oxonium monitoring method.

(12) The test method of prostate cancer according to (1), (2), (5) or (6), wherein the analysis uses an antibody or lectin.

(13) The test method of prostate cancer according to (12), wherein the method uses an antibody or lectin that specifically recognizes a saccharide having a multisialylated LacdiNAc structure.

(14) A test kit of prostate cancer, comprising an antibody or lectin that specifically recognizes a saccharide having a multisialylated LacdiNAc structure.

(15) The test kit of prostate cancer according to (14), wherein the saccharide having a multisialylated LacdiNAc structure is Glycan ID: 7512, Glycan ID: 7603, Glycan ID: 3401, or Glycan ID: 5602.

BRIEF DESCRIPTION OF DRAWINGS

FIG. 1 is a diagram showing sugar chain structure analysis of PSA using an oxonium monitoring method.

FIG. 2 is a diagram showing sugar chain analysis of PSA clinical samples.

FIG. 3 is a diagram showing the results with PSA G-index.

FIG. 4 is a diagram showing sugar chains capable of classifying the grade (malignancy) of prostate cancer.

FIG. 5 is a diagram showing the analysis results by lectin tissue staining.

DESCRIPTION OF EMBODIMENTS

Figure 1A:
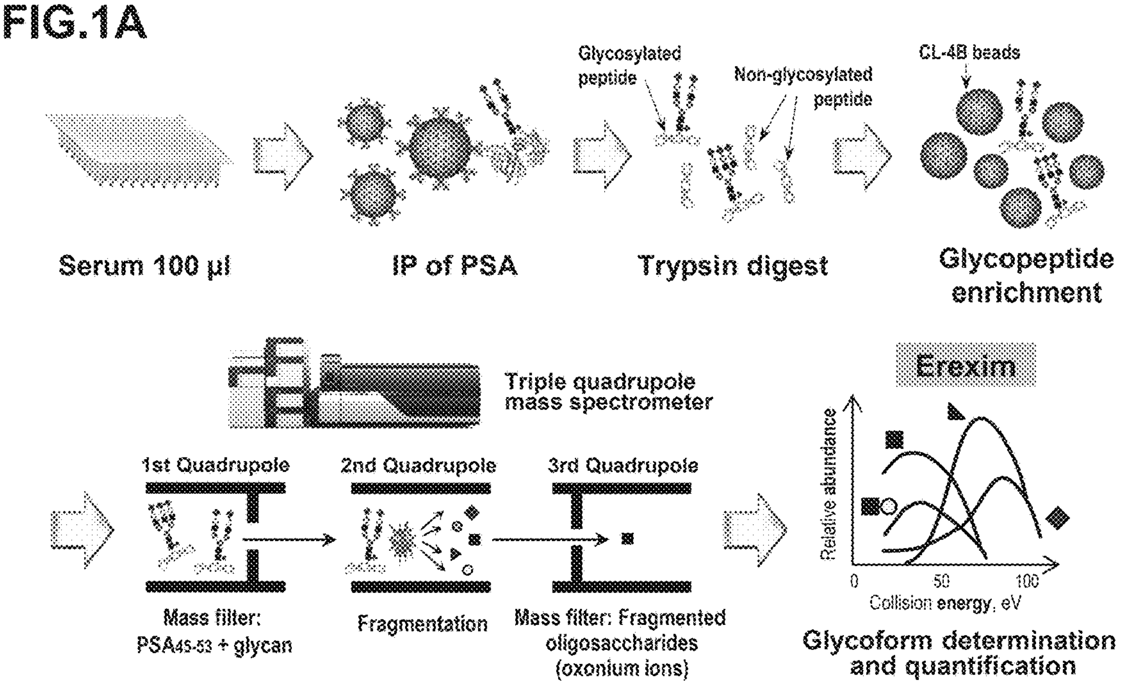
FIG. 1A shows an overview of the oxonium monitoring method.

The analysis by the present inventors has revealed that there is a significant increase in certain sugar chains having LacdiNAc (GalNAcβ1-4GlcNAc, N-acetylgalactosamine-N-acetylglucosamine) structure in patients suffering from prostate cancer. The analysis has been performed by mass spectrometry, but any method can be used as long as it is possible to recognize or analyze the multisialylated LacdiNAc structure or the specific sugar chain indicated by Glycan ID below.

The analytical method by mass spectrometry is a method that can be examined with great sensitivity as shown below, but not limiting to mass spectrometry, the analysis can be performed using anything that recognizes a particular sugar chain, such as an antibody, lectin, or aptamer which recognizes a multisialylated LacdiNAc structure. When the detection is performed with an antibody, the detection may be performed by any method used in the art, such as ELISA or SPR. When the detection is performed with a lectin, the detection may be performed by any method such as lectin blot or capillary electrophoresis. As shown in the Examples below, lectins such as WFA or MAM does not specifically recognize a multisialylated LacdiNAc structure. However, a system capable of specifically detecting a multisialylated LacdiNAc structure can be created by using several lectins in combination.

The present invention can be also carried out not only by analysis of relative abundances of Glycan ID: 7512 and Glycan ID: 7603, but also by profile recognition on profiling data of saccharides containing a multisialylated LacdiNAc structure. Specifically, profiles of multiple sugar chains obtained from patients having diagnosis determined prostate cancer are machine-learned by a computer as training data, and used it as a diagnostic support system. Then, during the test, by inputting the profile obtained from the subject as it is, prostate cancer candidate data may be detected by pattern recognition.

As shown in the Examples below, as a result of analyzing sugar chain structures modifying PSA, it has been revealed that prostate cancer can be detected with high accuracy by using PSA G-index defined below. Examination with PSA G-index on patients of a gray zone in conventional PSA tests as a secondary screening makes it possible to detect patients suffering from prostate cancer in a non-invasive manner. Further details are described below with showing data.

First, whether sugar chains modifying PSA are able to be sensitively detected and quantified was confirmed with PSA standard. PSA obtained from human semen was dissolved in 8 M urea, 50 mM HEPES-NaOH, pH 8.0, reduced with 10 mM DTT (GE Healthcare Life Science), alkylated with 25 mM iodoacetamide (Sigma-Aldrich), and then digested with Trypsin/Lys-C mix (Promega Corporation). Glycoproteins were enriched by hydrophilic purification method (Non Patent Literature 7), and dried in vacuo.

The resulting glycoproteins were analyzed by oxonium ion monitoring method (Erexim method, Non Patent Literature 8, Patent Literature 9) with a triple quadrupole mass spectrometer LCMS-8060 (Shimadzu Corporation) coupled with a Prominence nanoflow liquid chromatogram to identify sugar chains.

FIG. 1A schematically shows an overview of the oxonium ion monitoring method applied by multiple-reaction monitoring mass spectrometry (MRM-MS). PSA is degraded with trypsin into a mixture of peptides and glycopeptides, and they are separated with a nanoflow liquid chromatogram. In a mass spectrometer, glycopeptide ions having a particular mass are isolated at the first quadrupole (Q1). The isolated glycopeptide ions are introduced into the second quadrupole (Q2), and cause collision induced dissociation (CID). In the third quadrupole (Q3), oxonium ions from saccharides are selectively detected with a filter. Under optimal collision energy conditions, oxonium ions of m/z 138.1 function as quantitative reporters of glycopeptides of various saccharide compositions.

Figure 1B:
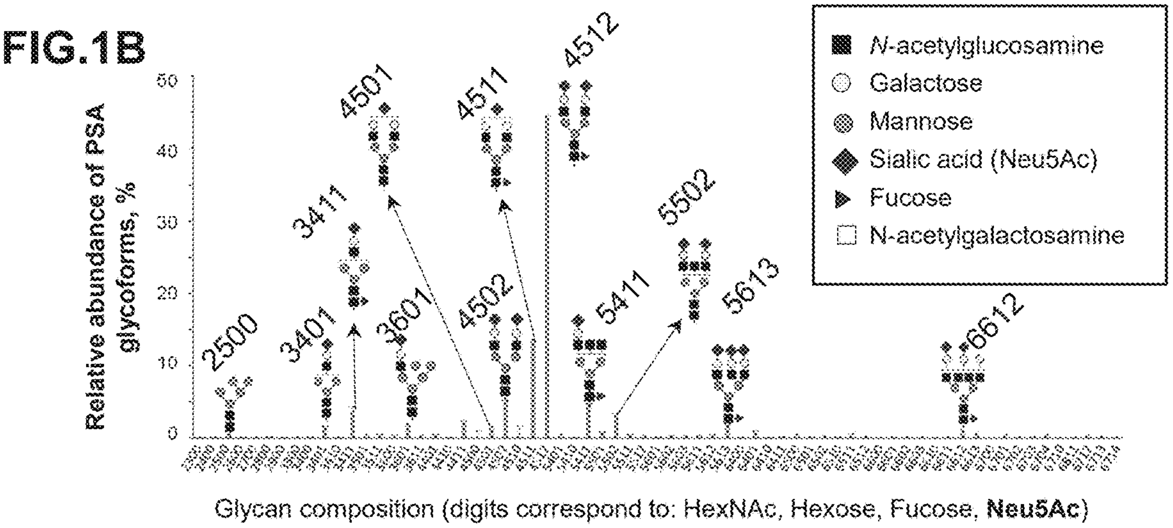
FIGS. 1B and 1C show the analysis results with PSA standard.

The results of performing sugar chain structure analysis with 100 ng of PSA standard obtained from human semen are shown in FIG. 1B. The digits on the horizontal axis in the figure define the type of each glycan as Glycan ID, and correspond to the numbers of HexNAc, Hexose, Fucose, and Neu5Ac from the left, respectively. The type and quantitative distribution of saccharides modifying asparagine at position 45 of PSA were analyzed. As a result, it was revealed by oxonium ion monitoring method that there were 67 types of saccharide structures.

Oxonium ion monitoring method has been found to be not only a method with which the analysis was completed in a short time of 25 minutes of LS/MS operation time without the need for enzymatic separation of glycans or chemical modification, but also a very sensitive detection method. The saccharide of the highest content was 4[HexNAc]5[Hex]1[Fuc]2[Neu5Ac](Glycan ID: 4512, 44.5±0.9%), and the saccharide of the lowest content was 6[Hex]7[NAcHex]0[Fuc]0[Neu5Ac](Glycan ID: 6700, 0.01±0.001%). There has been previously no report of detecting such a very large number of types of saccharides as 67 types of glycans modifying PSA, or detecting a very small amount of saccharide as 0.01%. Thus, it has been shown that oxonium ion monitoring method is a very sensitive method.

Figure 1C:
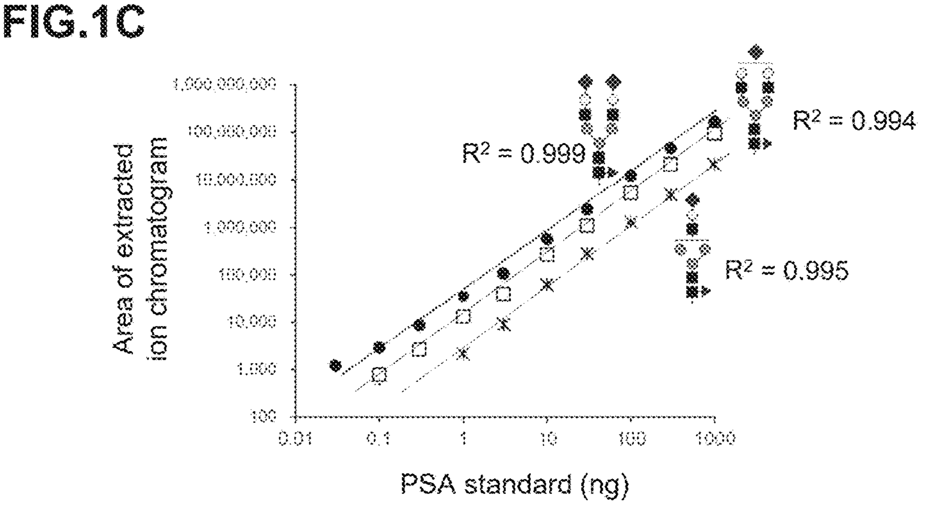

FIG. 1C shows the dynamic range of PSA sugar chain analysis. PSA digested with trypsin was serially diluted, and the detection limit was analyzed. As a result, it was possible to detect up to 1 fmol of the glycopeptide obtained from 0.03 ng of PSA, and the quantitative dynamic range was 5 digits or more ($R^2$>0.99). This result indicates that sugar chain analysis by oxonium ion monitoring method can perform test sufficiently even with PSA in a gray zone of 4 to 10 ng/ml.

Next, sugar chain analysis of PSA was performed using samples obtained from 15 prostate cancer patients and 15 prostatic hypertrophy patients having a PSA value in a gray zone, 4 to 10 ng/ml, to determine an index identifying prostate cancer, as a training set. Table 1 shows patient characteristics in the training set.

Analysis with clinical samples uses serum samples of prostate cancer patients and prostatic hypertrophy patients. It should be noted that final diagnosis is determined from histopathological diagnosis by prostate biopsy. Purification of PSA was performed as follows. To the serum was added 4-fold amount of wash solution (0.1% Tween-20 in PBS). The obtained solution was mixed with Protein G Sepharose to which anti-PSA monoclonal antibodies were immobilized (Fitzgerald), reacted overnight at 4° C., and washed. Then, PSA was eluted with 8 M urea, 50 mM HEPES-NaOH, pH 8.0, and purified. The eluted protein was reduced with 10 mM DTT, alkylated with 25 mM iodoacetamide, and then digested with Trypsin/Lys-C mix. Glycoproteins were enriched by hydrophilic purification method (Non Patent Literature 7), and dried in vacuo. It should be noted that, although serum samples were used here, not only blood derived samples but also urine can be used as samples.

TABLE 1

| | Training set | | Validation sample set | |
|---|---|---|---|---|
| Characteristics | Prostate cancer | Prostatic hypertrophy | Prostate cancer | Prostatic hypertrophy |
| Number of patients | 15 | 15 | 15 | 15 |
| Age, Mean ± SD (range) | 69.1 ± 6.69 (53-79) | 68.1 ± 5.0 (60-79) | 70.3 ± 3.3 (65-75) | 69.9 ± 6.4 (58-79) |
| PSA (ng/mL) Mean ± SD (range) | 7.5 ± 1.6 (4.19-9.76) | 7.4 ± 1.5 (4.31-9.36) | 7.5 ± 1.5 (5.41-9.67) | 7.5 ± 1.4 (5.32-9.43) |
| f/T PSA (%) Mean ± SD (range) | 16.0 ± 6.4 (8.4-34.2) | 20.8 ± 7.7 (9.8-45.1) | 16.1 ± 5.9 (9.2-27.8) | 19.3 ± 7.5 (9.8-34.0) |

Figure 2A:
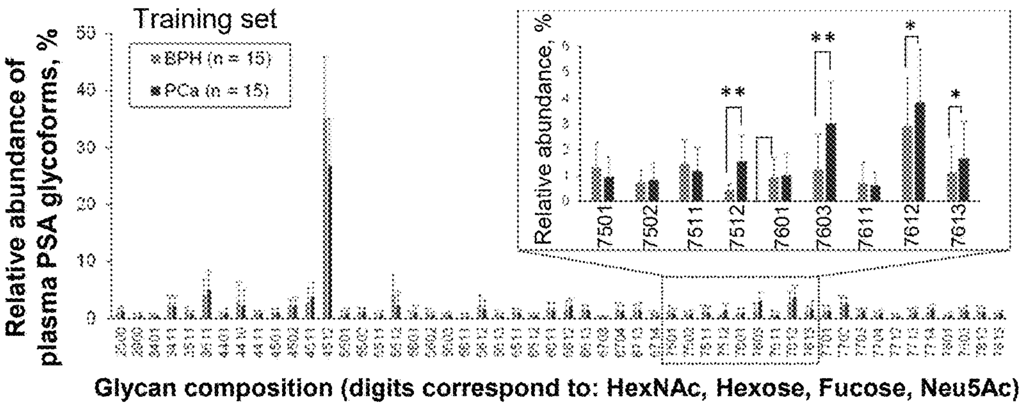
FIG. 2A shows types and abundance of sugar chains detected in a prostatic hypertrophy patient group and a prostate cancer patient group of a training set.
Figure 2B:
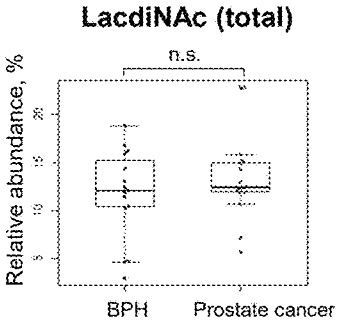
FIGS. 2B to 2D show relative abundances of sugar chains having a LacdiNAc structure detected in the prostatic hypertrophy patient group and the prostate cancer patient group.
Figure 2C:
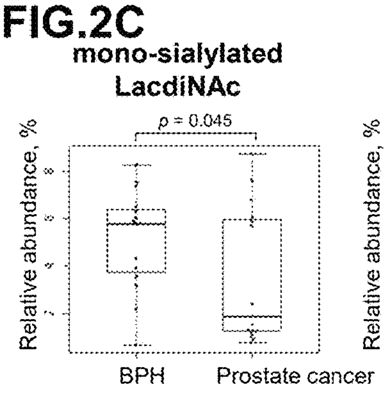
Figure 2D:
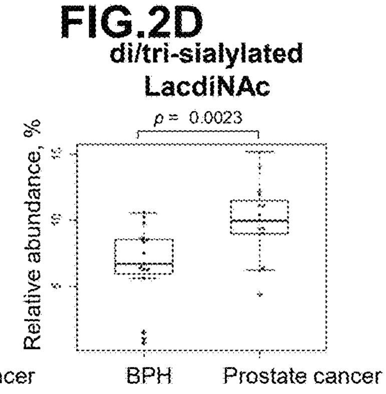
Figure 2E:
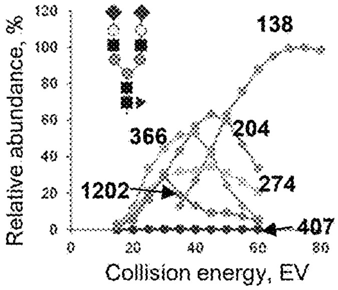
FIGS. 2E and 2F show the results of Erexim® analysis of representative sugar chains modifying PSA in serum of prostate cancer patients.
Figure 2F:
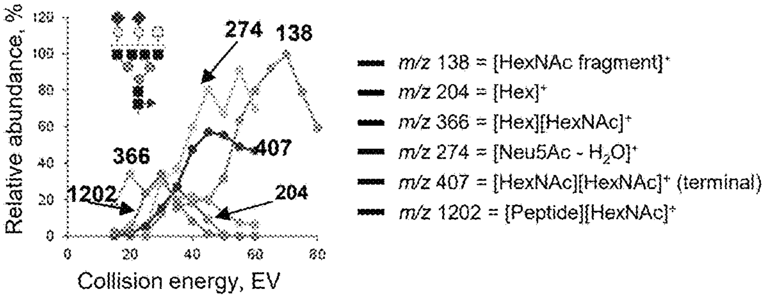

In the same manner as described above, 52 sugar chain structures on PSA could be quantified (FIG. 2A). Sugar chain structures of Glycan ID: 7512, 7603, 7612, and 7613 showed significant quantitative differences between the prostatic hypertrophy patient group and the prostate cancer patient group. It has also been found that sugar chains modifying PSA differ between the prostate cancer patient group and the healthy subject group, although no data is shown here. Thus, it is possible to distinguish prostate cancer patients from others, namely patients suffering from prostate diseases other than prostate cancer and healthy subjects, by analyzing sugar chain structures.

Among the 52 types of sugar chains, sugar chains containing a multisialylated structure, specifically di-/tri-sialylated LacdiNAc (GalNAcβ1-4GlcNAc), were significantly increased in the prostate cancer patient group compared to the prostatic hypertrophy patient group (FIG. 2 (D), p=0.0023). Meanwhile, the total amount of sialylated LacdiNAc (FIG. 2B) or sugar chain structures to which monosialylated LacdiNAc is attached (FIG. 2C) did not show significant changes between the prostatic hypertrophy patient group and the prostate cancer patient group. The terminal LacdiNAc structure and the presence of sialic acid (Neu5Ac) residues were also confirmed by Erexim method (FIGS. 2E and 2F).

Figure 3A:
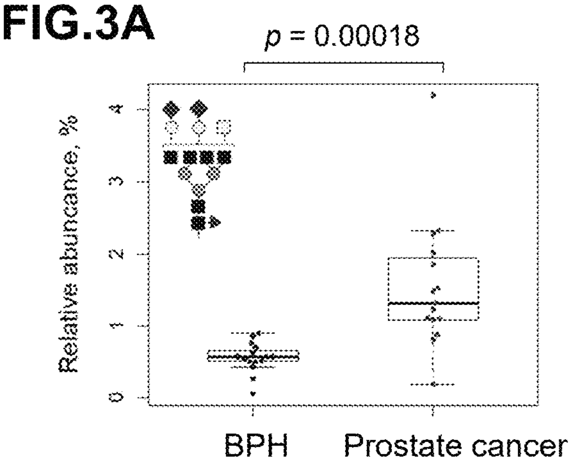
FIG. 3A shows relative abundances of Glycan ID: 7512 in a prostatic hypertrophy patient group and a prostate cancer patient group
Figure 3B:
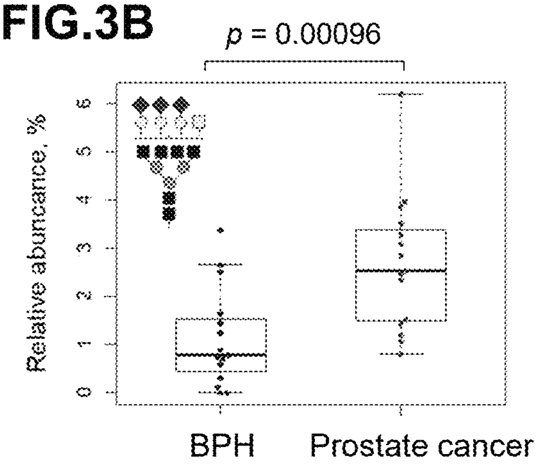
FIG. 3B shows relative abundances of Glycan ID: 7603 in the prostatic hypertrophy patient group and the prostate cancer patient group.

Based on these findings, we aimed to establish a novel diagnostic algorithm that complements the specificity of PSA test and can reliably reduce false positive rates. Two sugar chain structures specific for prostate cancer, Glycan ID: 7512 ($p=9.91\times10^{-8}$) and Glycan ID: 7603 ($p=1.66\times10^{-5}$), which showed significant differences between the prostate cancer patient group and the prostatic hypertrophy patient group in the training set, were selected, and the relative abundance thereof were plotted. FIG. 3A shows the relative abundances of Glycan ID: 7512 in prostatic hypertrophy patients (BPH) and prostate cancer patients, and FIG. 3B shows the relative abundances of Glycan ID: 7603 in those. Both Glycan ID: 7512 and 7603 show significant difference in abundance between them.

Based on these results, a diagnostic model (PSA G-index) based on logistic regression was established. In formula 1, p represents a value of PSA G-index; $x_1$ represents a relative abundance of Glycan ID: 7512; and $x_2$ represents a relative abundance of Glycan ID: 7603.

[Expression 3]

$$\log_e(p/(1-p)) = -5.85 + 4.72x_1 + 0.80x_2 \quad \text{(Formula 1)}$$

Figure 3C:
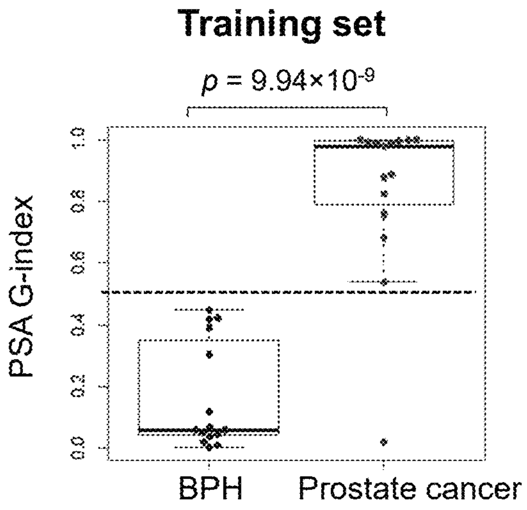
FIG. 3C shows a plot of PSA G-index values for the prostatic hypertrophy patient group and the prostate cancer patient group of a training set.

When a cutoff value of PSA G-index was set to 0.5, the sensitivity and specificity of the training set were 93.3% and 100%, respectively (FIG. 3C). It should be noted that, since PSA G-index is based on logistic analysis, the formula may differ slightly depending on the increase in the number of specimens to be analyzed in the future. However, it is possible to identify prostate cancer and other prostate diseases with high sensitivity and specificity by detecting Glycan ID: 7512 and Glycan ID: 7603 and using their amounts for identification.

Although all the saccharides modifying PSA are analyzed and their relative amounts are determined here, analysis may be performed of only a particular saccharide, such as a saccharide having a multisialylated LacdiNAc structure. In addition, among the peptides of PSA, peptides in the region that is not glycosylated may be taken as a reference, and a ratio of PSA modified by a particular saccharide to total PSA may then be determined to use for analysis. Although the relative values of saccharides described above differ depending on the saccharide used as a reference or the amount of PSA, the amounts of the saccharides are significantly different in prostate cancer and other prostate diseases, and thus it is possible to distinguish prostate cancer and other prostate diseases with high sensitivity by logistic analysis.

Figure 3D:
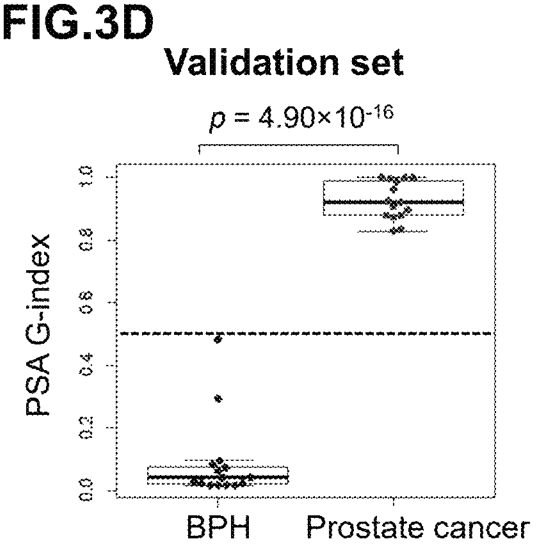
FIG. 3D shows a plot of PSA G-index values for the prostatic hypertrophy patient group and the prostate cancer patient group of a validation set.
Figure 3E:
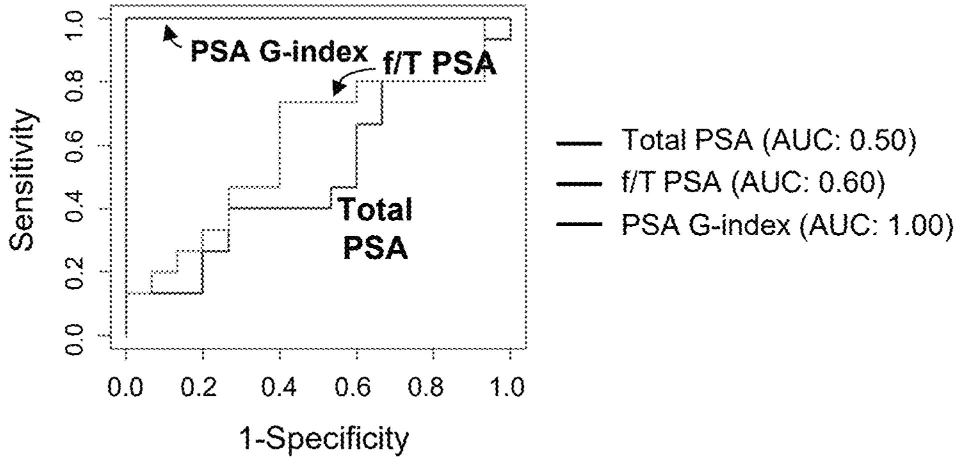
FIG. 3E shows ROC curves with PSA, PSA f/T, and PSA G-index values. It should be noted that Glycan ID defines the type of glycan, and the digits correspond to the numbers of HexNAc, Hexose, Fucose, and Neu5Ac from the left, respectively, which are described later in detail.

The PSA G-index was then evaluated using the validation sample set of Table 1 (FIG. 3D). All clinical samples were diagnosed as correct disease in both of the 15-case prostatic hypertrophy patient group and the 15-case prostate cancer patient group. In ROC curve analysis, the PSA G-index area under the curve (AUC) was 1.00 (100% sensitivity and 100% specificity), while AUCs of the PSA value (Total PSA) and the ratio of free PSA to total PSA (PSA f/T) were 0.50 (80.0% sensitivity, 33.3% specificity) and 0.60 (73.3% sensitivity, 60.0% specificity), respectively (FIG. 3E). These results indicate that PSA G-index can significantly improve specificity of prostate cancer diagnosis and avoid false positives compared to PSA or PSA f/T values, which are conventionally indexes of prostate cancer.

Next, whether sugar chain structures on PSA in serum reflect the grade (malignancy) of prostate cancer was analyzed. Using serum from 77 patients of different grades shown in Table 2, sugar chain analysis by oxonium ion monitoring method was performed.

TABLE 2

| Characteristics | Prostatic hypertrophy | GS6 | GS7 | GS8 | GS9 |
|---|---|---|---|---|---|
| Number of patients (range) | 30 | 8 | 23 | 11 | 5 |
| Age, Mean ± SD (range) | 69.1 ± 5.8 (58-79) | 73.8 ± 3.4 (67-79) | 68.9 ± 5.2 (53-78) | 72.5 ± 4.5 (67-78) | 75.2 ± 6.2 (65-84) |
| PSA (ng/mL) Mean ± SD (range) | 7.4 ± 1.4 (4.31-9.43) | 9.7 ± 4.7 (5.57-21.14) | 10.7 ± 7.0 (5.5-27.85) | 14.9 ± 1.4 (5.41-28.67) | 50.8 ± 33.9 (6.88-107.54) |
| f/T PSA (%) Mean ± SD (range) | 20.1 ± 7.6 (9.8-45.1) | 19.5 ± 8.9 (6.3-34.2) | 14.2 ± 5.6 (7.0-26.7) | 14.8 ± 8.3 (9.3-34.9) | 11.7 ± 6.2 (7.3-24.1) |

Figure 4A:
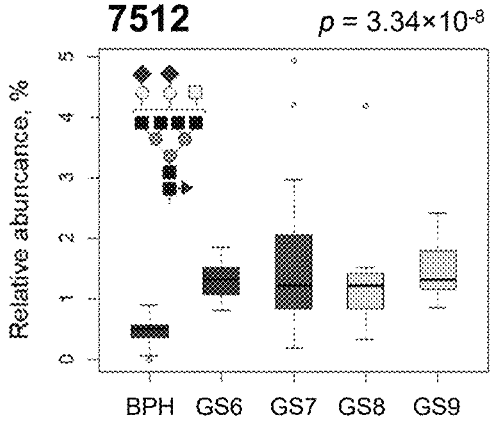
FIGS. 4A, 4B, 4C, and 4D show correlations of Glycan ID: 7512, Glycan ID: 7603, Glycan ID: 3401, and Glycan ID: 5602, with a Gleason score, respectively.
Figure 4B:
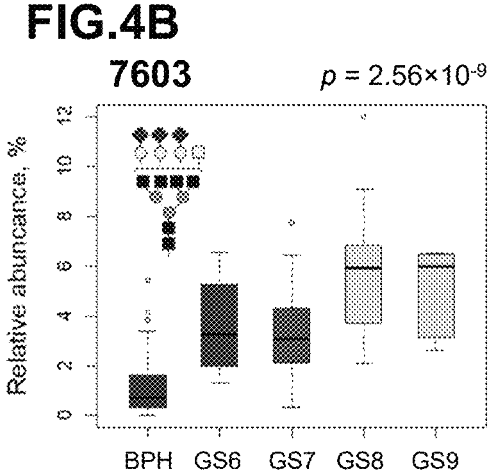

As a result, the frequency of Glycan ID: 7512 (FIG. 4A) or Glycan ID: 7603 (FIG. 4B), which are sugar chain structure to which multiple sialylated LacdiNAc are attached, was positively correlated with Gleason score (GS), an index of malignancy by prostate biopsy ($p=3.34\times10^{-8}$, or $p=2.56\times10^{-9}$). The Gleason score is an index that classifies the malignancy of prostate cancer that occurs with different degrees of malignancy in the same prostate. The Gleason score is classified into 9 stages of GS2 to GS10 by the sum of the values obtained by determining predominant and ancillary lesions from biopsy. The higher the Gleason score value indicates the higher the malignancy.

Figure 4C:
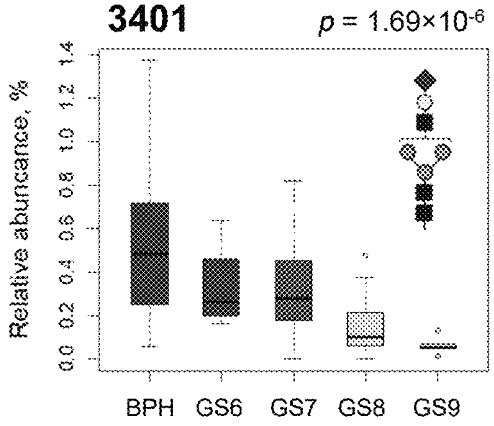
Figure 4D:
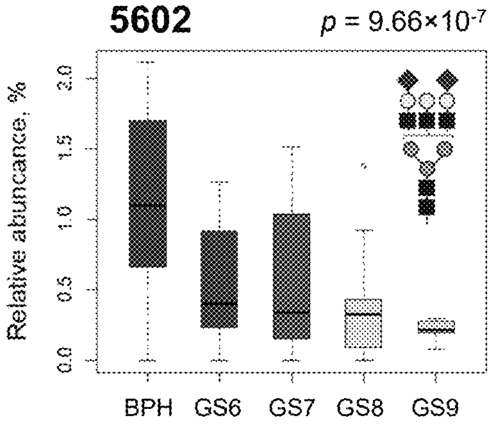

Furthermore, Glycan ID: 3401 (FIG. 4C) or Glycan ID: 5602 (FIG. 4D) showed a negative correlation with the Gleason score ($p=1.69\times10^{-6}$, or $p=9.66\times10^{-7}$). These results indicate the possibility that the pathological malignancy of prostate cancer is correlated with the amounts of certain sugar chains, and the malignancy of prostate cancer can be diagnosed by liquid biopsy.

Figure 5A:
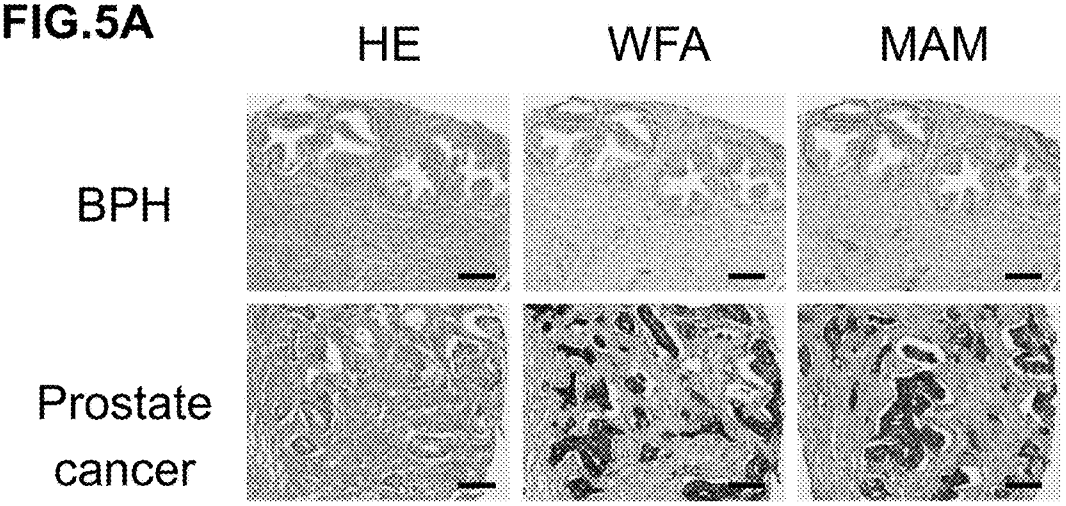
FIG. 5A shows prostate tissue staining results with HE, WFA, and MAM in prostatic hypertrophy patients and prostate cancer patients.
Figure 5B:
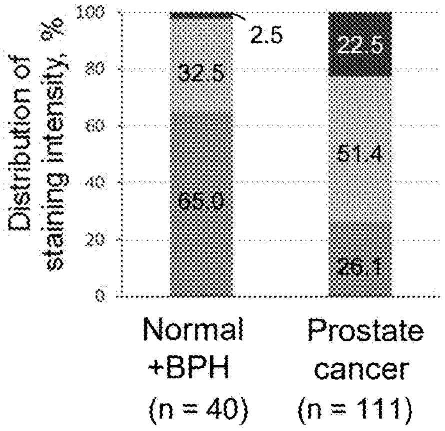
FIG. 5B shows prostate tissue staining intensity with WFA in prostatic hypertrophy patients and prostate cancer patients.
Figure 5C:
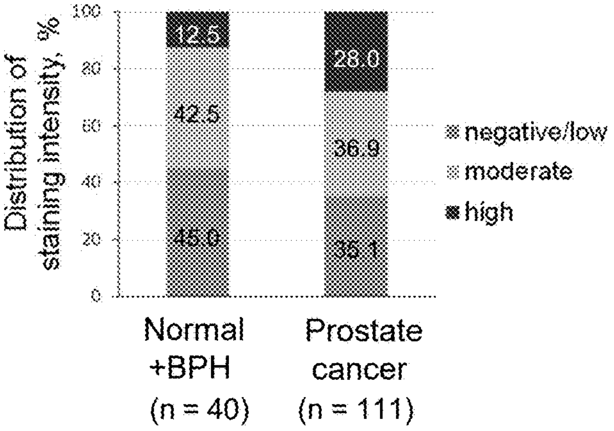
FIG. 5C shows prostate tissue staining intensity with MAM in prostatic hypertrophy patients and prostate cancer patients.

To identify the cause of the increase of multisialylated LacdiNAc structure in serum PSA, lectin histochemical staining was performed using a tissue microarray (US Biomax) containing 9, 31, and 111 prostate tissues of normal, prostatic hypertrophy patients, and prostate cancer patients, respectively. Histochemical staining was performed using WFA, a lectin that detects a LacdiNAc structure, or MAM, a lectin that detects a Siaα2-3Gal structure. Biotinylated lectins were used for both WFA and MAM, and the analysis was performed using a Vectastain Elite ABC kit (Vector Laboratories). As a result, cytoplasmic and protoplasmic membranes of cancer cells were significantly stained (FIG. 5A). The staining intensity was classified into three levels, "high", "moderate", and "low", and the stained images of tissues of prostate cancer patients and those of normal and prostatic hypertrophy patients were compared. In the prostate cancer tissues, images of "high" in staining intensity were observed at a high frequency of 9.00-fold when stained with WFA and 2.24-fold when stained with MAM (FIGS. 5B, 5C).

WFA and MAM lectins specifically recognize GalNAc structures containing a LacdiNAc structure and a Neu5Acα2-3Gal structure, respectively. The above results indicate that prostate cancer tissue tends to strongly express glycoproteins containing LacdiNAc and Neu5Ac structures. These histological findings were consistent with the results of PSA sugar chain structure analysis by mass spectrometry. Accordingly, it is possible to determine prostate cancer, and even the stage of prostate cancer, by analyzing sugar chains of PSA in blood without performing tissue biopsy.

INDUSTRIAL APPLICABILITY

Test using the diagnostic marker, PSA G-index, shown in the Examples, performed as a secondary screening of patients diagnosed as having a suspected prostate cancer from the PSA value, can identify prostate cancer with good specificity. The test can identify even prostate cancer at an early stage with good specificity, which makes it possible to lead to early treatment.

The invention claimed is:

1. A method for detecting prostate cancer and other prostate diseases comprising:

obtaining a specimen including PSA from a subject;

isolating at least one multisialylated LacdiNAc structure from the PSA in the specimen;

detecting and quantifying the isolated multisialylated LacdiNAc structure using mass spectrometry with an energy-resolved oxonium ion monitoring method;

determining whether or not an abundance of the multisialylated LacdiNAc structure is above a predetermined value;

distinguishing between prostate cancer and other prostate diseases based on whether or not the abundance of the multisialylated LacdiNAc structure is above the predetermined value; and identifying that the subject has prostate cancer when the abundance of the multisialylated LacdiNAc structure is above the predetermined value; and identifying that the subject has other prostate disease when the abundance of the multisialyated LacdiNAc structure is below the predetermined value.

2. The method for detecting prostate cancer and other prostate diseases according to claim 1, further comprising:

isolating at least one of Glycan ID: 7512, Glycan ID 7603, Glycan ID 7612, or Glycan ID 7613 from the PSA in the specimen, wherein the determining whether or not the abundance of the multisialylated LacdiNAc structure is above the predetermined value includes:

measuring, as the abundance of the multisialylated LacdiNAc structure, relative abundance(s) of Glycan ID: 7512, Glycan ID: 7603, Glycan ID: 7612, and/or Glycan ID: 7613.

3. The method for detecting prostate cancer and other prostate diseases according to claim 2, wherein the relative abundances of Glycan ID: 7512 and Glycan ID: 7603 are calculated by logistic analysis.

4. The method for detecting prostate cancer and other prostate diseases according to claim 2, comprising:

substituting the relative abundances of Glycan ID: 7512 and Glycan ID: 7603 into the following formula 1:

[Expression 1]

$$\log_a\left(p/(1-p)\right) = -5.85 + 4.72x_1 + 0.80x_2 \text{ (式1)} \qquad \text{(Formula 1)}$$

wherein p represents a value of PSA G-index; $x_1$ represents a relative abundance of Glycan ID: 7512, and $x_2$ represents a relative abundance of Glycan ID: 7603.

5. The method for detecting prostate cancer and other prostate diseases according to claim 1, wherein the specimen is blood, serum, plasma, or urine.

6. The test method for detecting prostate cancer and other prostate diseases according to claim 1, wherein the specimen is a specimen obtained from a patient having a PSA value of 4 to 10 ng/ml.

7. A method for detecting a grade of prostate cancer, comprising:

obtaining a specimen including PSA from a subject;

isolating at least one of Glycan ID: 7512, Glycan ID: 7603, Glycan ID: 3401 or Glycan ID: 5602 from the PSA in the specimen;

detecting and quantifying multisialylated LacdiNAc structure by detecting the isolated at least one of Glycan ID: 7512, Glycan ID: 7603, Glycan ID: 3401 or Glycan ID: 5602 using mass spectrometry with an energy-resolved oxonium ion monitoring method;

distinguishing between prostate cancer and other prostate diseases based on relative abundance(s) of the at least one of Glycan ID: 7512, Glycan ID: 7603, Glycan ID: 3401, or Glycan ID: 5602; and determining the grade of prostate cancer based on the relative abundance(s), the grade of prostate cancer being one of a Gleason score of GS6 to GS9.

8. The method for detecting according to claim 7, wherein the specimen is blood, serum, plasma, or urine.

9. The method detecting prostate cancer according to claim 1, wherein the specimen is serum.

10. The method according to claim 7, wherein the specimen is serum.

11. The method for detecting prostate cancer according to claim 1, wherein the other prostate diseases include prostatic hypertrophy.

12. The method according to claim 7, wherein the other prostate diseases include prostatic hypertrophy.

* * * * *